United States Patent [19]

Hsiao et al.

[11] Patent Number: 5,744,620
[45] Date of Patent: Apr. 28, 1998

[54] CATALYTIC OXIDATION OF CYCLIC OLEFINS

[75] Inventors: Yu-Ling Hsiao, Bridgeville, Pa.; Harry B. Gray, Pasadena; Jay A. Labinger, Claremont, both of Calif.

[73] Assignee: Bayer Corporation, Pittsburgh, Pa.

[21] Appl. No.: 890,869

[22] Filed: Jul. 10, 1997

[51] Int. Cl.$^6$ ............................................. C07D 301/06
[52] U.S. Cl. ............................................. 549/533
[58] Field of Search ............................................. 549/533

[56] References Cited

U.S. PATENT DOCUMENTS

| | | | |
|---|---|---|---|
| 5,142,070 | 8/1992 | Fullington et al. | 549/532 |
| 5,347,057 | 9/1994 | Khan | 568/910 |
| 5,420,314 | 5/1995 | Katsuki et al. | 549/533 |

FOREIGN PATENT DOCUMENTS

96/24601  8/1996  WIPO.

OTHER PUBLICATIONS

Journal of the Chemical Society, Chemical Communictions pp. 186–187, 1974 (ACS), Paulson et al.
Journal of Molecular Catalysis A: Chemical vol. 104, pp. L119–L122, 1995, Birnbaum et al.
Tetrahedron, vol. 52, pp. 515–530, 1996, Hamada et al.
Journal of American Chem. Soc., vol. 112, 1990, pp. 2801–2803, Zhang et al.
Chemistry Letters, pp. 1661–1664, 1990, Mukaiyama et al.
Journal of Organic Chemistry, vol. 41, No. 8, pp. 1384–1389, 1976, Budnik et al.
Industrial and Engineering Chemistry Research, vol. 34, pp. 2298–2304 1995, Hayashi et al.
Tetrahedron Letters, vol. 36, pp. 159–162, 1995, Reddy et al.
Journal of Molecular Catalysis A: Chemical, vol. 113, pp. 191–200 1996, Böttcher et al.

*Primary Examiner*—Bernard Dentz
*Attorney, Agent, or Firm*—Joseph C. Gil; Aron Preis

[57] ABSTRACT

A catalyzed process whereby a cyclic olefin is oxidized to produce an epoxide is disclosed. The inventive process which uses air, or molecular oxygen as the sole oxidizing agent, and which is catalyzed by a specifically structured metallosalen complex is characterized in its high selectivity and high turnover efficiency.

10 Claims, No Drawings

CATALYTIC OXIDATION OF CYCLIC OLEFINS

FIELD OF THE INVENTION

The present invention relates to the catalytic oxidation of cyclic olefins and more particularly to a process wherein molecular oxygen or air is the sole oxidizing agent.

SUMMARY OF THE INVENTION

A catalyzed process whereby a cyclic olefin is oxidized to produce an epoxide is disclosed. The inventive process which uses air, or molecular oxygen as the sole oxidizing agent, and which is catalyzed by a specifically structured metallosalen complex is characterized in its high selectivity and high turnover efficiency.

BACKGROUND OF THE INVENTION

A simple, one-step synthesis of epoxides has long been among the objectives for the researchers in academic fields as well as industry. The most direct and economical method for introducing oxygen into a molecule employs molecular oxygen, yet few methods achieve this goal. The art is noted to include U.S. Pat. No. 5,142,070 which disclosed is a process for the direct oxidation of propylene to propylene oxide. Noncatalytic processes of gas phase oxidation of alkenes using molecular oxygen have been reported. These processes involve large energy inputs and are characterized by their low yields. The catalytic oxidation methods for alkenes generally require a stoichiometric amount of oxidants or a combination of molecular oxygen and co-reductants. For example, the uses of metalloporphyrin and metallosalen catalysts such as Fe(TPP)Cl and Mn(salen)Cl with a costly non-regenerative oxidants such as iodosyl benzene, sodium hypochloride, alkyl hydroperoxides, etc. have been reported. In this connection mention is made of the disclosure of catalytic autoxidation by metalloporphyrins made by Paulson et al., in Journal of the Chemical Society, Chemical Communication pages 186– 186, issued 1974 (ACS), and of the disclosed mechanism of catalytic alkene oxidation by molecular oxygen and halogenated iron porphyrins, by Birnbaum et al. in Journal of Molecular Catalysis A: Chemical Vol. 104, pages L119–L122, issued 1995.

Also relevant in this connection are the following publications:

(i) "Mechanism of one oxygen atom transfer from oxo (salen) manganese(V) complex to olefins" Hamada et al., Tetrahedron Vol. 52, pages 515–530, issued 1996;

(ii) "Enantioselective Epoxidation of unfunctionalized olefins catalyzed by (Salen)manganese complexes" by Zhang et al. in the Journal of the American Chemical Society Vol. 112, pages 2801–2803, issued 1990;

(iii) "Nickel(II) complex-catalyzed epoxidation of olefins with molecular oxygen and primary alcohol" by Mukaiyama et al. in Chemistry Letters pages 1661–1663, issued 1991, and (iv) "Epoxidation of olefins with molecular oxygen in the presence of cobalt complexes" by Budnik et al. in Journal of Organic Chemistry Vol. 41, pages 1384–1389, issued 1976. The cobalt complexes disclosed by Budnik are non-salen.

Also relevant is the article "Formation of propylene oxide by the gas-phase reaction of propane and propene mixture with oxygen" by Hayashi et al. published in 1995 in Industrial & Engineering Chemistry Research Vol. 34, pages 2298–2304 as is the article entitled "Aerobic oxidation of hydrocarbons catalyzed by electronegative iron salen complexes" by Boettcher et al., in Journal of Molecular Catalysis A; Chemical Vol. 1 13, pages 191–200, 1996.

The cobalt compounds disclosed in "Cobalt catalyzed oxidation of cyclic alkenes with molecular oxygen; Allylic oxidation versus double bond attack" by Reddy et al. in Tetrahedron Letter Vol. 36, pages 159–162, 1995, are structurally different from the metallosalen compounds of the present invention.

U.S. Pat. No. 5,347,057 is noted for its disclosure of a method for the oxidation of alkanes and cycloalkanes, to form mostly alcohols, in the presence of air or oxygen and a ruthenium metal complex catalyst. U.S. Pat. No. 5,420,314 is noted to have disclosed a process for the asymmetric epoxidation of olefins using an optically active manganese complex.

Close art is represented by PCT WO 96/24601 which disclosed the use of salen-based metal complexes in the oxidation of alkenes in the presence of an oxidizing agent or a combination of oxygen and a sacrificial co-reductant.

DETAILED DESCRIPTION OF THE INVENTION

In accordance with the present invention, a liquid phase, catalyzed oxidation process of cyclic olefins is carried out. The process wherein air, or molecular oxygen, is the sole oxidizing reactant and where the catalyst is a specifically structured metallosalen complex, is characterized in its high selectivity and high turnover efficiency.

Direct oxidation of cyclic olefins, exemplified schematically below by reference to cyclohexene, in accordance with the inventive process yields a product mix which includes mostly epoxide, alcohol, and ketone.

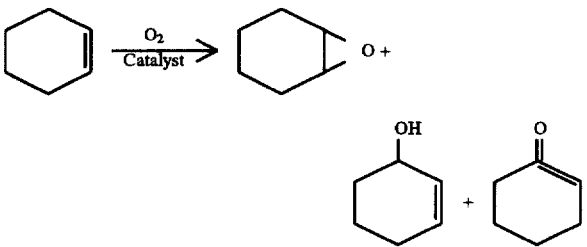

The present invention resides in part, in the findings that air, or molecular oxygen, may be used as the sole oxidation reactant and that the use of a particular salen-based compound yields a mix of products which is epoxide-rich.

The olefins suitable in the process of the invention are compounds which contain at least one cyclic olefin. Included are cyclopentene, cyclohexene, cycloheptene, cyclooctene and norbornene. A preferred olefin is cyclohexene.

The catalyst suitable in the inventive process is a metal salen complex the structure of which conforms to

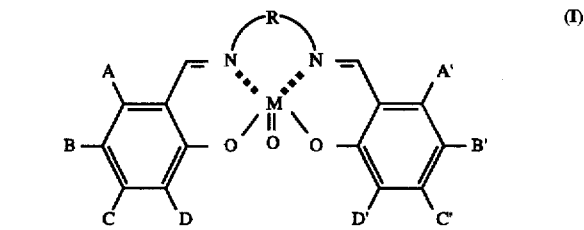

(I)

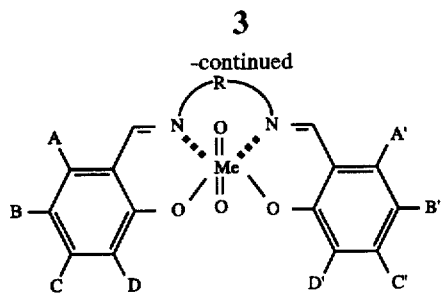

wherein M denotes a member selected from the group consisting of Cr and V, preferably V and wherein Me denotes a member selected from the group consisting of Mo, Nb, W, Re, and Os, preferably Mo, and wherein R is an aliphatic chain, straight or branched, cyclic or aromatic moiety containing 2 to 30 carbons, optionally containing 1 to 10 heteroatom selected from the group consisting of N, O, F, Cl, and Br. A, A', B, B', C, C', D and D' independently denote hydrogen, F, Cl, Br, $NO_2$, $SO_3R$, or CN.

Among the examples of the moiety referred to as R, mention may be made of ethylene, 1,2-diphenylethylene, 1,1'-binaphthyl, cyclohexyl, phenyl, naphthyl, and dichlorophenyl groups.

EXPERIMENTAL

1. A Vanadium complex conforming to formula (I) was prepared by first synthesizing of a salen ligand (Ligand A) and using it to prepare the catalyst.

Ligand-A-N,N'-Bis(3,5-dinitrosalicylidene)-1,2-diphenylethylenediamine was thus prepared: 2.4 g of 3,5-Dinitrosalicylaldehyde was dissolved in 250 mL absolute ethanol to form a yellow solution followed by the addition of a solution containing 1.2 g of 1,2-Diphenylethylenediamine in 250 mL absolute ethanol to form a reaction mixture. A red precipitate was formed immediately after the additions. The reaction mixture was heated to just below the boiling point of ethanol for an hour, and then allowed to cool down and placed in the freezer over night followed by filtering and methanol wash. The resulting product-N,N'-Bis(3,5-dinitro-salicylidene)-1,2-diphenylethylenediamine-(1.636 g) in the form of a red powder was obtained after filtration, methanol wash and drying under vacuum at room temperature for 5 hours.

Preparation of a vanadium-salen complex: 400 mg salen ligand-A was dissolved in 75 mL absolute ethanol and 10 mL nitromethane to form an orange ligand solution. A solution containing $V(acac)_2$ (20 mol % excess) in 15 ml of absolute ethanol was added to the ligand solution dropwise to form a reaction mixture with a dark brown precipitate. The reaction mixture was heated to just below the boiling point of ethanol for an hour and was then cooled down and placed in the freezer. The resulting vanadium catalyst (metal salen complex) in the form of a brown powder was obtained after filtration, methanol wash and drying under vacuum at room temperature for 5 hours.

Corresponding Mo and Ru catalysts, corresponding to structures (II) and (I) respectively, were prepared following substantially the same procedure. The Cobalt, and iron salen catalysts which were used in the comparative examples conform respectively to

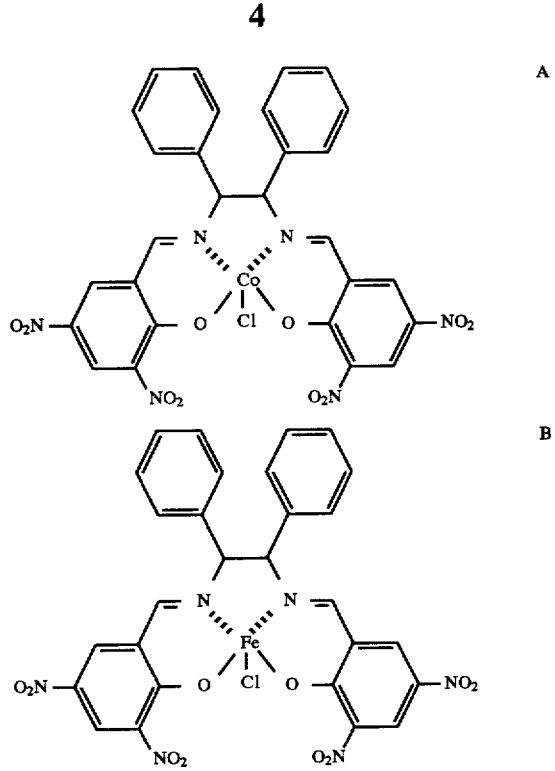

Experiments were conducted to determine the efficacy of the catalysts in the inventive process. There were three procedures used in these determinations:

Procedure A:

15 mL of dry acetonitrile and 3 mg of salen metal catalyst were placed in a 100 mL round-bottom flask fitted with a condenser. Oxygen was bubbled through the liquid and flushed throughout the system for ca. 10 min. Freshly distilled cyclohexene was first bubbled with oxygen and 1 mL of this oxygen-purged cyclohexene was then added to the flask. The reaction was allowed to reflux for 7 hours.

Procedure B:

15 mL of the oxygen-purged cyclohexene was placed in a three-neck-round bottomed flask fitted with a condenser. 3 mg of the salen metal catalyst was added to the liquid. The mixture was then heated up to refluxing temperature of cyclohexene (83° C.) for 7 hours.

Procedure C:

15 mL of dry acetonitrile and 3 mg of salen metal catalyst were placed in a 100 mL round-bottom flask fitted with a condenser. Oxygen was bubbled through the liquid and flushed throughout the system for ca. 10 min. Freshly distilled cyclohexene was first bubbled with oxygen and 1 mL of this oxygen-purged cyclohexene was then added to the flask. 0.89 mL of the sacrificial co-reductant, isobutyraldehyde was added to the mixture. The reaction was allowed to reflux for 7 hours.

The table below summarizes the results of the experiments using the indicated procedures and salen metal catalysts. The process described above as Procedure A was used in evaluating the efficacy of the Co, Ru, Fe and V salen metal complexes; Procedure B was used in the evaluation of the V and Mo complexes. Procedure C was used in the evaluation of Co, Ru and V salen metal complexes. The compositional makeup of the product mix was determined by gas chromatography.

| Salen metal catalyst | Procedure | Oxidation Products Selectivity (%) | | |
|---|---|---|---|---|
| | | epoxide | alcohol | ketone |
| Co | A | 15.6 | 23.0 | 61.4 |
| Co | C | 67.1 | 19.1 | 13.8 |
| Ru | A | 26.4 | 25.6 | 48.0 |
| Ru | C | 76.3 | 12.7 | 11.0 |
| Fe | A | 10.6 | 26.9 | 62.5 |
| V | A | 61.4 | 28.3 | 10.3 |
| V | B | 51.3 | 38.0 | 10.6 |
| V | C | 86.3 | 5.5 | 8.2 |
| Mo | B | 53.8 | 43.5 | 2.7 |

The use of Co, Ru or Fe metal salen catalyst in a process where molecular oxygen is the sole oxidizing agent yields a product mix which is low in epoxide content. Surprisingly, the inventive process which is catalyzed by the metal salen complexes of the invention yields a product mix which is relatively high in its epoxide content. To obtain high yield of epoxide in a process using Co or Ru salen catalysts, it is necessary to use a sacrificial co-reductant in conjunction with molecular oxygen. The results clearly show that the oxidation products selectivity strongly depends on the type of metal in the salen-based metal complexes. The inventive process yields a product mix where the epoxide selectivity is greater than that of ketone and that of alcohol.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing an epoxide comprising reacting a cyclic olefin with a sole oxidizing agent selected from the group consisting of air and molecular oxygen, in the presence of a catalyst selected from the group consisting of metal salen complex the structure of which conforms to

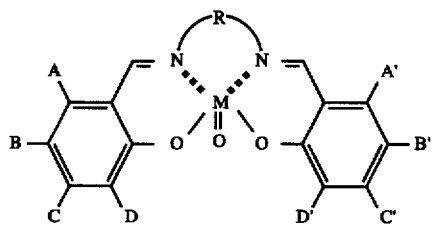

(I)

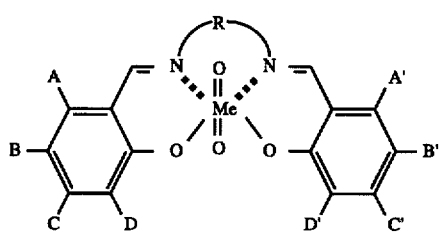

(II)

wherein M denotes a member selected from the group consisting of Cr and V, and wherein Me denotes a member selected from the group consisting of Mo, Nb, W, Re, and Os, wherein R is an aliphatic chain, straight or branched, cyclic or aromatic moiety containing 2 to 30 carbons, and wherein A, A', B, B', C, C', D and D' independently denote a member selected from the group consisting of hydrogen, F, Cl, Br, $-NO_2$, $-SO_3R$, or $-CN$.

2. The process of claim 1 wherein said metal salen complex conforms structurally to

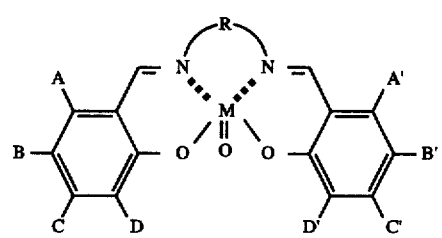

(I)

3. The process of claim 1 wherein said metal salen complex conforms structurally to

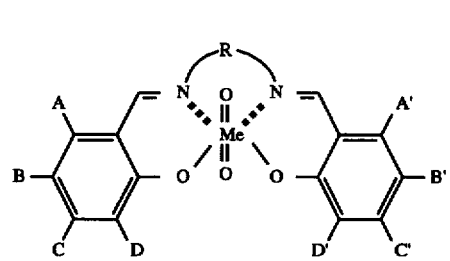

(II)

4. The process of claim 1 wherein said cyclic olefin is a member selected from the group consisting of cyclopentene, cyclohexene, cycloheptene, cyclooctene and norbornene.

5. The process of claim 1 wherein said cyclic olefin is cyclohexene.

6. The process of claim 1 wherein said R further contains 1 to 10 heteroatom selected from the group consisting of N, O, F, Cl, and Br.

7. The process of claim 1 wherein M denotes V.

8. The process of claim 3 wherein Me denotes Mo.

9. The process of claim 7 wherein cyclic olefin is cyclohexene.

10. The process of claim 8 wherein cyclic olefin is cyclohexene.

* * * * *

UNITED STATES PATENT AND TRADEMARK OFFICE
CERTIFICATE OF CORRECTION

PATENT NO. : 5,744,620
DATED : April 28, 1998
INVENTOR(S) : Yu-Ling Hsiao, Harry B. Gray, Jay A. Labinger It is certified that error appears in the above-indentified patent and that said Letters Patent is hereby corrected as shown below:

On the title page: Item [73]           should include both
Bayer Corporation,           , Pittsburgh, PA          and
--California Institute of Technology, 1200 East California
          Pasadena, CA          --

Signed and Sealed this

Tenth Day of November 1998

*Attest:*

BRUCE LEHMAN

*Attesting Officer*        Commissioner of Patents and Trademarks